United States Patent [19]

Babb

[11] Patent Number: 5,206,422

[45] Date of Patent: Apr. 27, 1993

[54] PROCESS FOR PREPARATION OF FLUORINATED CARBONYL COMPOUNDS

[75] Inventor: David A. Babb, Lake Jackson, Tex.

[73] Assignee: The Dow Chemical Company, Midland, Mich.

[21] Appl. No.: 775,326

[22] Filed: Oct. 11, 1991

[51] Int. Cl.$^5$ .................... C07C 69/63; C07C 53/21
[52] U.S. Cl. .................................. 560/227; 562/605
[58] Field of Search .................. 560/227; 562/605

[56] References Cited

U.S. PATENT DOCUMENTS 4,357,282 11/1982 Anderson et al. .................. 560/227

Primary Examiner—Jose' G. Dees
Assistant Examiner—Keith MacMillan
Attorney, Agent, or Firm—John A. Langworthy

[57] ABSTRACT

A process for the preparation of fluorinated carbonyl compounds from a fluorinated methyl or ethyl ether using tin tetrachloride as a catalyst. The fluorinated ether is contacted with the tin tetrachloride catalyst at a temperature between 0° C. and 250° C.

24 Claims, No Drawings

PROCESS FOR PREPARATION OF FLUORINATED CARBONYL COMPOUNDS

FIELD OF THE INVENTION

This invention relates to a process for the preparation of fluorinated carbonyl compounds, and the products of such process.

BACKGROUND OF THE INVENTION

A fluorinated carbonyl compound can be prepared from a fluorinated methyl or ethyl ether. In the case of a primary ether, an acylated product results, while in the case of a secondary ether, a ketone results. The reaction of formation involves contacting the fluorinated ether with an appropriate catalyst in a reaction mixture which typically is heated. A solvent may be added to the reaction mixture where desirable.

Numerous catalysts have been proposed for use in such a reaction. Anderson, U.S. Pat. No. 4,357,282, explores the suitability of many catalysts for such purpose, among which is tin tetrachloride (stannic chloride, $SnCl_4$). It is reported in this reference that when tin tetrachloride is used as a catalyst in this type of a carbonyl-forming reaction, the reaction shows an initial period of activity but then becomes sluggish. This drop in the rate of reaction is attributed to progressive fluorination of the tin tetrachloride.

As tin tetrachloride is a relatively inexpensive material, it would be advantageous to determine a process whereby it could be used efficiently and reliably as a catalyst for the formation of fluorinated carbonyl compounds from a fluorinated methyl or ethyl ether.

SUMMARY OF THE INVENTION

In one aspect, this invention involves a process for preparing a fluorinated carbonyl compound, including (a) contacting a fluorinated ether which is generally described by formula as follows:

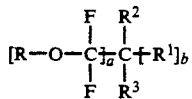

where
R is a methyl or ethyl radical:
$R^1$ is —F, —Cl, —Br, —$SO_2F$, —COF, —$OCH_3$, —CN, —$CO_2H$, —$CO_2CH_3$, —$OC_6F_5$, or —OX, —SX, or —X, where —X is a linear or branched fluorinated alkyl radical of 1 to 8 carbon atoms, interruptible with either oxygen or keto groups, and optionally containing functional substituents selected from the group consisting of —F, —Cl, —Br, —$SO_2F$, —COF, —$OCH_3$, —CN, —$CO_2H$, —$CO_2CH_3$ and —$OC_6F_5$;
$R^2$ is —H or —F;
$R^3$ is —F or —$CF_3$;
a is 1 or 2;
b is 0 or 1; and
a+b is 2
in a reaction mixture with tin tetrachloride at a temperature in the range of about 0° C. to about 250° C.; and (b) recovering a fluorinated carbonyl compound in at least a 35 weight percent yield.

In another aspect, this invention involves a process for preparing a fluorinated carbonyl compound, including (a) contacting a fluorinated ether, as described by the formula set forth above, in a reaction mixture with tin tetrachloride at a first temperature which is at least about 90 percent of the boiling point of the fluorinated ether, until fluorinated carbonyl product begins to form: (b) heating said reaction mixture at a second temperature which is lower than said first temperature: and (c) recovering a fluorinated carbonyl compound.

In yet another aspect, this invention involves a process for preparing a fluorinated carbonyl compound, including (a) contacting a fluorinated ether, as described by the formula set forth above, in a reaction mixture with $SnCl_xF_y$, where x and y are each independently 1, 2 or 3, and x+y=4, at a temperature in the range of about 0° C. to about 250° C.; and (b) recovering a fluorinated carbonyl compound.

This invention involves a process for the preparation of fluorinated carbonyl compounds from a fluorinated methyl or ethyl ether using tin tetrachloride as a catalyst, and the products of such process. The fluorinated ether is contacted with the tin tetrachloride catalyst at a temperature between 0° C. and 250° C. In a preferred embodiment, a reaction mixture of a fluorinated ether and tin tetrachloride is heated until fluorinated derivatives of the tin tetrachloride are formed, after which the carbonyl-forming reaction proceeds rapidly.

The process of this invention is useful for the preparation of fluorinated carbonyl compounds, particularly formyl esters. These carbonyl compounds may be used to prepare unsaturated ethers which may be copolymerized with other unsaturated, halogenated monomers (such as tetrafluoroethylene) to obtain polymers suitable for fabrication into films, membranes and other finished goods.

DETAILED DESCRIPTION OF THE INVENTION

By the process of this invention, fluorinated carbonyl compounds can be prepared from a fluorinated methyl or ethyl ether. The fluorinated ethers suitable for use in the process of this invention are described generally by the formula set forth above.

A preferred group of ethers is made up of those ethers where $R^1$ is —$CO_2CH_3$, and a particularly preferred ether is $CH_3O[CF_2]_2CO_2CH_3$, methyl 3-methoxy tetrafluoropropanoate (sometimes referred to below as "EE", short for "ether-ester").

A fluorinated ether as described above may be prepared, for example, by the addition of an alkoxy ion to a fluorinated olefin and subsequent addition of the intermediate resulting therefrom to a diester. Other known methods are disclosed in Anderson, U.S. Pat. No. 4,357,282.

The fluorinated carbonyl product resulting from the process of this invention may be described generally by the formula

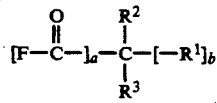

where $R^1$, $R^2$, $R^3$, a and b are as set forth above. A methyl or ethyl fluoride is split out as the carbonyl bond is formed.

In the practice of this invention, a fluorinated ether, as described above, is contacted with tin tetrachloride as a catalyst. This operation can be performed (a) at a temperature in the range of about 0° C. to about 250° C.

when the molar concentration of tin tetrachloride catalyst to fluorinated ether is in the range of about 1:50 to about 1:1, (b) at a temperature in the range of about 50° C. to about 150° C. when the molar concentration of tin tetrachloride catalyst to fluorinated ether is in the range of about 1:33.3 to about 1:5, and (c) at a temperature in the range of about 70° C. to about 140° C. when the molar concentration of tin tetrachloride catalyst to fluorinated ether is in the range of about 1:25 to about 1:10.

The reaction between the fluorinated ether and the tin tetrachloride catalyst is endothermic, unlike the reaction between a fluorinated ether and certain other catalysts such as $TiCl_4$. The reaction mixture catalyzed by tin tetrachloride must therefore be heated at or above a first temperature during a period of induction heating before formation of the carbonyl compound will begin. This initial formation of carbonyl compound is typically detected by commencement of the evolution of gas, which can be chloro- or fluoromethane, chloro- or fluoroethane and/or the fluorinated carbonyl product. This period of induction heating is typically at least thirty minutes, but, depending on the proportions of reactants used and which ether is used, the induction heating may require a period of at least forty-five or at least sixty minutes.

A first temperature can be selected which is approximately the boiling point of the fluorinated ether, or is lower than the boiling point of the fluorinated ether, but it is preferred that the first temperature be at least 90 percent, and more preferably be at least 95 percent of the boiling point of the fluorinated ether. For example, a first temperature of at least 130° C., or preferably at least 140° C., is typically suitable when performing induction heating on a fluorinated ether such as methyl 3-methoxy tetrafluoropropanoate. However, when induction heating does not occur at a high enough temperature, the reaction will not proceed. Again with reference to methyl 3-methoxy tetrafluoropropanoate, heating same at 110° C. for 2 hours has been found to be completely ineffective to start the carbonyl-forming reaction.

Once a sufficient period of induction heating has occurred and the reaction to form the fluorinated carbonyl product has commenced, the formation reaction will proceed vigorously until the supply of either the fluorinated ether or the tin tetrachloride is exhausted. Despite the length of time required for the induction heating, the formation reaction will, once started, proceed vigorously at a second temperature which can be (a) in the range of about 50 to about 90 percent of the first temperature, or (b) preferably in the range of about 60 to about 80 percent of the first temperature. The second temperature can, for example, be approximately the boiling point of the fluorinated carbonyl product. Surprisingly, no sluggishness is observed in the reaction once it commences, and no problem of solubility of the catalyst arises.

At this second temperature, provided that the tin tetrachloride catalyst is always present in the reaction mixture at at least a concentration of about 2 mole percent (based on the moles of fluorinated ether starting material), any fluorinated ether present in the reaction vessel after induction heating has been completed is converted to fluorinated carbonyl compound at a rate of at least about 0.3 moles per hour, preferably at least about 0.5 moles per hour, and more preferably at least about 0.8 moles per hour (each rate being measured per mole of fluorinated ether present as starting material), and all such fluorinated ether present is converted without decrease in the rate.

A solvent may be used in the reaction mixture if desired. Numerous materials which were evaluated for use as a solvent were found to suffer from various problems which included reactivity with the tin tetrachloride catalyst or immiscibility with the reaction product. Among those solvents were sulfolane, diglyme, diphenyl ether, dimethylformamide, decane, and silicone oil. Solvents which were found to be non-reactive with the ether, the catalyst or the carbonyl product, and therefore useful in the process of this invention, include perfluoro tetradecahydrophenanthrene, 1,1,2,2- tetrachloroethane, and 1,2-dichlorobenzene. A solvent may be used in an amount which allows complete intermixing of the fluorinated ether and the catalyst throughout the entire course of the reaction. This assists in control of the rate of the reaction. If a solvent is used, the first temperature can be at least 90 percent, and preferably is at least 95 percent, of the boiling point of the lower boiling of the fluorinated ether or the solvent.

The fluorinated carbonyl product is condensed and collected, and can be fractionally redistilled, by known methods. The process of this invention produces the carbonyl product in a yield by weight of at least 35 percent, however the yield is preferably at least 70 percent, more preferably at least 80 percent, and most preferably at least 90 percent by weight.

When the reaction is completed, a solid residue is left in the reaction vessel. This residue is one or more fluorinated forms of tin tetrachloride, the bulk of the residue being $SnF_4$. The tin tetrachloride catalyst becomes fluorinated by the heating during the formation reaction, most of it progressively becoming completely fluorinated. While not wishing to be bound by any particular theory, it appears that a threshold degree of fluorination is achieved by the extended period of induction heating, after which the reaction to form the carbonyl compound begins and proceeds rapidly. Not only does fluorination of the tin tetrachloride catalyst cause no sluggishness or solubility problems in the reaction, the presence of fluorinated catalyst in the residue suggests that the reaction will not start until a threshold level of fluorination is attained. Consequently, one could, if desired, use $SnCl_xF_y$, where $x$ and $y$ are each independently 1, 2 or 3, and $x+y=4$, as the catalyst in the process of this invention.

The formation reaction can be run at atmospheric pressure, or in a closed vessel where an autogenous pressure of up to 100 atmospheres may develop.

ILLUSTRATIVE EMBODIMENTS

To illustrate the practice of this invention, exam of several preferred embodiments are set forth below. It is not intended, however, that these examples (Examples 1–9) should in any manner restrict the scope of this invention. Some of the particularly desirable features of this invention may be seen by contrasting the characteristics of Examples 1–9 with those of various controlled formulations (Controls A and B) which do not possess the features of, and are not therefore embodiments of, this invention.

Analysis of product formed in the following reactions was performed on a Varian 3700 gas chromatograph using a capillary column coupled to a flame ionization detector.

EXAMPLE 1

Methyl-2,2,3,3-tetrafluoro-3-methoxypropionate ["EE", (42.89 g, 0.23 mole)] is placed in a nitrogen purged 100 ml 3-necked round bottomed flask containing a magnetic stirring bar and fitted with a distilling head, a rubber septum and a thermometer. A nitrogen pad is maintained in the reaction flask as tin tetrachloride (3.07 g, 0.012 mole) is injected via syringe into the reaction vessel. The mixture is stirred and heated to 130° C. where the starting material begins to reflux. Condensed vapors are refluxed back into the reaction mixture. As fluoromethane begins to evolve as a gas, and the overhead temperature drops to 90° C., the condensate is collected in a receiving flask. In this manner, the reaction mixture is distilled to dryness, leaving 6.79 g of powdered residue in the reaction vessel. The distillate (31.03 g) contains 93% methyl difluoro(fluoroformyl)-acetate, as determined by gas chromatographic analysis. This represents an 82% isolated yield of the pure product.

EXAMPLE 2

An oven dried 50 ml 3-necked round bottom flask is fitted with a clean rubber septum, a reflux condenser and a thermometer. A dry magnetic stirring bar is placed in the flask, the flask is placed in an electric heating mantle and secured in the fume hood over a magnetic stirrer. A sample of EE (14.9 g, 10.5 ml, 78.4 mmole) is drawn into a syringe and injected into the reaction vessel under a dry nitrogen purge. Stannic chloride (1.02 g, 0.46 ml, 3.9 mmole) is added to the reaction vessel via syringe through the rubber septum. This represents approximately a 5 percent (moles of catalyst per moles of EE) catalyst concentration. The reaction mixture is heated to reflux (140° C.). Progress of the conversion of EE is monitored by removing a 1 microliter sample every 10 to 15 minutes for gas chromatographic analysis. After 30 minutes the reaction mixture begins to turn brown and evolve gas very quickly. Gas chromatographic analysis at 40 minutes shows a 37 percent conversion of the EE starting material. Analysis at 70 minutes indicates 100 percent conversion of the EE, with the major component of the reaction mixture (96.6 area %) being methyl-2-fluorocarbonyl-2,2-difluoroacetate [methyl malonyl fluoride ("MMF")].

EXAMPLE 3

The procedure of Example 2 is repeated except that 21 ml (157 mmole) EE is mixed with 0.73 ml (1.63 g, 6.28 mmole) tin tetrachloride. This represents approximately a 4 mole percent catalyst concentration. After 80 minutes of stirring at 135° C., this results in a 90 percent conversion of EE to MMF.

EXAMPLE 4

The procedure of Example 2 is repeated except that 10.5 ml (78.5 mmole) EE is mixed with 0.27 ml (0.61 g, 2.34 mmole) tin tetrachloride. This represents approximately a 3 mole percent catalyst concentration. After 2 hours of stirring at 135° C., this results in a 95 percent conversion of EE to MMF.

EXAMPLE 5

The procedure of Example 2 is repeated except that 10.5 ml (78.5 mmole) EE is mixed with 0.18 ml (0.41 g, 1.57 mmole) tin tetrachloride. This represents approximately a 2 mole percent catalyst concentration. After 3 hours of stirring at 135° C., this results in a 35 percent conversion of EE to MMF.

CONTROL A

The procedure of Example 2 is repeated except that 10.5 ml (78.5 mmole) EE is mixed with 0.09 ml (0.205 g, 0.785 mmole) tin tetrachloride. This represents approximately a 1 mole percent catalyst concentration. After 2 hours of stirring at 135° C., no conversion of EE to MMF is observed.

CONTROL B

The procedure of Example 2 is repeated except that 10.5 ml (78.5 mmole) EE is mixed with 0.045 ml (0.1025 g, 0.3925 mmole) tin tetrachloride. This represents approximately a 0.5 mole percent catalyst concentration. After 2 hours of stirring at 135° C., no conversion of EE to MMF is observed.

Examples 2–5 and Controls A and B demonstrate that the tin tetrachloride catalyst must be present in the reaction mixture in at least an amount of about 2 mole percent, relative to the moles of fluorinated ether, before fluorinated carbonyl product is obtained.

EXAMPLE 6

The procedure of Example 3 is repeated except that when the reaction nears completion at 95 minutes, 0.5 equivalent of EE (10.5 ml, 78.5 mmole) is added to the reaction mixture via syringe through the septum. When the reaction again nears completion at 185 minutes, another 0.5 equivalent of EE is added to the reaction vessel. The overall catalyst concentration is approximately 2 percent.

Example 6 demonstrates that the tin tetrachloride catalyst successfully converts 37 equivalents of EE for each equivalent of tin tetrachloride.

EXAMPLE 7

A solution of 1,2-dichlorobenzene (o-DCB, 25 ml) and EE (5.08 g) is placed in a 100 ml, three-necked round bottom flask containing a magnetic stirring bar and equipped with a thermometer, rubber septum and short path distilling head. A nitrogen pad is applied to the distilling head and is routed through a dry ice/isopropanol trap and then to a gas bubbler. Tin tetrachloride (2.7 ml, 6.05 g) is added to the reaction flask via syringe through the septum. The mixture is heated to 140° C., at which point the initial amount of EE reacts smoothly, generating gas and cooling the reaction temperature to 132° C. Heating is continued as the MMF product begins to distill. The remaining amount of EE is then pumped into the reaction vessel by syringe pump at a rate of 60 ml per hour, until 65.64 g of EE has been added. At this point, the distillation of MMF product begins to slow as the catalyst dies out, so 1.0 g of tin tetrachloride is added to the mixture. As the reaction starts again, an additional 15.45 g of EE is pumped into the reaction vessel. The temperature of the reaction mixture is maintained at 143° C. as the product is distilled off at an overhead temperature range of 82°–92° C. In this manner, 64.73 g MMF is distilled from the reaction of 87.17 g of EE and 7.05 g of SnCl$_4$. This calculates to an 83.7% yield of MMF based on 92.3% conversion of EE.

EXAMPLE 8

Methyl-3-methoxy tetrafluoropropanoate ("EE") is is washed thoroughly with deionized water and stored over anhydrous MgSO$_4$ and CaSO$_4$ for at least three days. After a thorough purge of a round bottom flask reactor with dry nitrogen, o-dichlorobenzene (250 ml) is charged to the reactor through a 500 ml addition funnel. Tin tetrachloride (approx. 250 g) is then charged to the reactor through the addition funnel via syringe. EE (15 ml, 21 g) is then added to the reactor through the addition funnel as the reaction mixture is stirred with a mechanical stirrer. The mixture is heated to a steady temperature of 135° C. with constant stirring.

After a 45-60 minute induction period (stirring at 135° C.) the reaction begins, evolving chloromethane and fluoromethane gasses and driving MMF and EE over into a distillation receiver. The distillation receiver is initially set to total reflux until the overhead temperature comes down to 95° C.-100° C., at which point the receiver is diverted to the recovery flask and product is collected.

When the overhead temperature settles to 95° C.-100° C., the addition of more EE is begun. EE is added at a rate that maintains an overhead distillation temperature of between 90° C. and 105° C. When the overhead temperature exceeds 105° C., the EE feed is halted, and the distillation receiver is again diverted to total reflux until the overhead temperature settles back to 95° C.-100° C. The feed rate for EE is generally 3-5 ml/min.

Addition of EE is continued until a decrease in catalytic activity is noted, as evidenced by decreased gas evolution, decreased boil-up rate of distillate product, and eventually by a significant increase in the overhead temperature of the distillate (steady at 115°-125° C.). At this point, the feed of EE is halted, and the reactor temperature is allowed to rise to 150° C. to distill over any unreacted EE into the recovery flask. During this distillation, the overhead temperature generally rises to about 130° C.

A total of 777 g (4.09 moles) of EE is added to 251 g of tin tetrachloride in the reactor, according to this procedure, over a period of 3 hours. The reaction began after a 50 minute induction period of stirring at 135° C. The reactor temperature is maintained at 132° C. throughout the addition of EE. The overhead temperature is kept between 88° C. and 105° C., usually steady at 95° C. The recovered distillate weighed 654 g and represented a 92.9 percent yield of MMF based on an 86.3 percent conversion of EE.

EXAMPLE 9

A total of 1,249 g (6.57 moles) of EE is added to 254 g of tin tetrachloride in the reactor, according to the procedure of Example 8, over a period of 4 hours. The reaction began after a 65 minute induction period of stirring at 135° C. The reactor temperature is maintained at 130°-135° C. throughout the reaction. The recovered distillate weighed 1,038 g and represented a 92.0 percent yield of MMF based on an 85.7 percent conversion of EE.

The examples above all demonstrate that when fluorinated carbonyl compounds are prepared by contacting a fluorinated ether with tin tetrachloride as a catalyst, the fluorinated carbonyl product is obtained in an advantageously high yield, in many cases not less than 90 percent by weight. This is to be contrasted with the yield obtained when the formation reaction is run under conditions substantially similar to those described above using TiCl$_4$ as the catalyst. The yield from such titanium-catalyzed reactions is frequently not greater than 75 percent.

It is within the skill in the art to practice this invention in numerous modifications and variations in light of the above teachings. It is, therefore, to be understood that the various embodiments of this invention described herein may be altered without departing from the spirit and scope of this invention as defined by the appended claims.

What is claimed is:

1. A process for preparing a fluorinated carbonyl compound, comprising (a) contacting a fluorinated ether which is generally described by formula as follows:

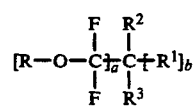

where
   R is a methyl or ethyl radical;
   R$^1$ is —F, —Cl, —Br, —SO$_2$F, —COF, —OCH$_3$, —CN, —CO$_2$H, —CO$_2$CH$_3$, —OC$_6$F$_5$, or —OR$^4$, —SR$^4$ or —R$^4$, where R$^4$ is a linear or branched fluorinated alkyl radical of 1 to 8 carbon atoms, interruptible with either oxygen or keto groups, and optionally selected from the group consisting of —F, —Cl, —Br, —SO$_2$F, —COF, —OCH$_3$, —CN, —CO$_2$H, —CO$_2$CH$_3$, —OC$_6$F$_5$;
   R$^2$ is —H or —F;
   R$^3$ is —F or —CF$_3$;
   a is 1 or 2;
   b is 0 or 1; and
   a+b is 2 in a reaction mixture with tin tetrachloride at a first temperature which is at least about 90 percent of the boiling point of the fluorinated ether, until fluorinated carbonyl product begins to form;

(b) upon the beginning of formation of fluorinated carbonyl product, heating said reaction mixture at a second temperature which is about 50 to about 90 percent of said first temperature; and (c) recovering a fluorinated carbonyl compound in at least a 35 weight percent yield.

2. The process of claim 1 wherein tin tetrachloride is present in said reaction mixture in an amount of at least 2 mole percent with reference to the moles of fluorinated ether.

3. The process of claim 1 wherein R$^1$ in said formula is —CO$_2$CH$_3$ and b is 1.

4. The process of claim 1 wherein said fluorinated ether is methyl 3-methoxy tetrafluoropropanoate.

5. The process of claim 1 wherein the reaction mixture includes a solvent.

6. The process of claim 1 wherein the solvent is 1,2-dichlorobenzene.

7. The process of claim 1 wherein the first temperature is at least about 130° C.

8. The process of claim 1 wherein the reaction mixture is heated at the first temperature for at least about thirty minutes.

9. The process of claim 1 wherein the second temperature is in the range of about 60 to about 80 percent of the first temperature.

10. The process of claim 1 wherein the second temperature is approximately the boiling point of the fluorinated carbonyl product.

11. The process of claim 1 wherein the fluorinated carbonyl compound recovered in step (c) is generally described by formula as follows:

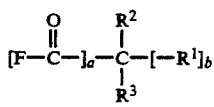

where $R^1$, $R^2$, $R^3$, a and b are as set forth in claim 1.

12. A process for preparing a fluorinated carbonyl compound, comprising
   (a) contacting a fluorinated ether, as described by the formula in claim 1, in a reaction mixture with $SnCl_xF_y$, where x and y are each independently 1, 2 or 3, and $x+y=4$, at a first temperature which is at least about 90 percent of the boiling point of the fluorinated ether, until fluorinated carbonyl product begins to form;
   (b) upon the beginning of formation of fluorinated carbonyl product, heating said reaction mixture at a second temperature which is about 50 to about 90 percent of said first temperature; and
   (c) recovering a fluorinated carbonyl compound.

13. The process of claim 12 wherein $R^1$ in said structural formula is $-CO_2CH_3$ and b is 1.

14. The process of claim 12 wherein said fluorinated ether is methyl 3-methoxy tetrafluoropropanoate.

15. The process of claim 12 wherein the reaction mixture further comprises a solvent.

16. The process of claim 12 wherein the fluorinated carbonyl compound recovered in step (c) is generally described by formula as follows:

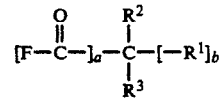

where $R^1$, $R^2$, $R^3$, a and b are as set forth in claim 1.

17. The process of claim 12 wherein $SnCl_xF_y$, where x and y are each independently 1, 2 or 3, and $x+y=4$, is present in said reaction mixture in an amount of at least 2 mole percent with reference to the moles of fluorinated ether.

18. The process of claim 15 wherein the solvent is 1,2-dichlorobenzene.

19. The process of claim 12 wherein the first temperature is at least about 130° C.

20. The process of claim 12 wherein the reaction mixture is heated at the first temperature for at lest about thirty minutes.

21. The process of claim 12 wherein the second temperature is in the range of about 60 to about 80 percent of the first temperature.

22. The process of claim 12 wherein the second temperature is approximately the boiling point of the fluorinated carbonyl product.

23. The process of claim 11 wherein the fluorinated carbonyl compound recovered in step (c) is methyl difluoro(fluoroformyl)acetate.

24. The process of claim 16 wherein the fluorinated carbonyl compound recovered in step (c) is methyl difluoro(fluoroformyl)acetate.

* * * * *

UNITED STATES PATENT AND TRADEMARK OFFICE
CERTIFICATE OF CORRECTION

PATENT NO. : 5,206,422
DATED : April 27, 1993
INVENTOR(S) : David A. Babb

It is certified that error appears in the above-indentified patent and that said Letters Patent is hereby corrected as shown below:

Column 8, line 32, claim 1, after "optionally" insert --containing functional substituents --.

Column 10, line 23, claim 20, "lest" should be --least--.

Signed and Sealed this

Nineteenth Day of July, 1994

Attest:

BRUCE LEHMAN

*Attesting Officer*     *Commissioner of Patents and Trademarks*